United States Patent
El-Sherif et al.

(10) Patent No.: US 10,466,096 B2
(45) Date of Patent: Nov. 5, 2019

(54) FIBER OPTIC HYDROPHONE SENSORS AND USES THEREOF

(71) Applicant: Drexel University, Philadelphia, PA (US)

(72) Inventors: Mahmoud A. El-Sherif, Blue Bell, PA (US); Afshin S. Daryoush, Bryn Mawr, PA (US); Peter A. Lewin, Wyndmoor, PA (US); Rupa Gopinath Minasamudram, Bangalore (IN)

(73) Assignee: Drexel University, Philadelphia, PA (US)

( * ) Notice: Subject to any disclaimer, the term of this patent is extended or adjusted under 35 U.S.C. 154(b) by 262 days.

(21) Appl. No.: 15/477,247

(22) Filed: Apr. 3, 2017

(65) Prior Publication Data

US 2017/0199076 A1    Jul. 13, 2017

Related U.S. Application Data

(63) Continuation-in-part of application No. 14/159,649, filed on Jan. 21, 2014, now Pat. No. 9,823,113, which
(Continued)

(51) Int. Cl.
*G02B 6/00* (2006.01)
*G01H 9/00* (2006.01)
(Continued)

(52) U.S. Cl.
CPC ............ *G01H 9/004* (2013.01); *A61B 8/4281* (2013.01); *G01L 11/025* (2013.01); *G01L 11/04* (2013.01);
(Continued)

(58) Field of Classification Search
CPC ....... G01H 9/004; G01L 11/04; G01L 11/025; A61B 8/4281; A61B 2562/0266; A61B 2562/0247; G02B 6/262
See application file for complete search history.

(56) References Cited

U.S. PATENT DOCUMENTS 4,799,752 A    1/1989 Carome
9,528,893 B2 *  12/2016 Wang .................. G01L 7/086
(Continued)

OTHER PUBLICATIONS

Afshin S. Daryoush, "RF and Microwave Photonic Techniques in Biomedical applications" Mar. 30, 2009-Apr. 1, 2009, Conference: Sarnoff Symposium, 2009. Sarnoff '09, IEEE, pp. 6 plus bibliography page.

(Continued)

*Primary Examiner* — Ellen E Kim
(74) *Attorney, Agent, or Firm* — Schott, P.C.

(57) ABSTRACT

A sensing method is based on using a special fiberoptic probe for detection of acoustic/ultrasound pressure in an immersion medium. The developed system is highly sensitive in detecting ultrasound waves up to 100 MHz, for imaging of micro structures and more. For applications up to 100 MHz, without spatial averaging corrections, the probe tip is modified by reducing the fiber diameter to 7 um or less. Also, to maximize acousto-optic interaction, the probe tip, not just its end face, may be coated with a thin layer of metallic material. This thin film coating satisfies partial transparency of the metallic coating. The coating thickness may range from 2 nm to 10 nm or others depending on the type of the coating material. The probe detects the pressure of acoustic and/or ultrasound waves propagating within an immersion medium, whenever the probe tip is immersed inside the medium, and having a reasonable immersion contact surface.

20 Claims, 11 Drawing Sheets

Related U.S. Application Data is a continuation of application No. 13/150,906, filed on Jun. 1, 2011, now Pat. No. 8,661,908.

(60) Provisional application No. 62/317,516, filed on Apr. 2, 2016, provisional application No. 61/350,422, filed on Jun. 1, 2010.

(51) Int. Cl.
 *G01L 11/02* (2006.01)
 *G01L 11/04* (2006.01)
 *A61B 8/00* (2006.01)
 *G02B 6/26* (2006.01)

(52) U.S. Cl.
 CPC ........... *A61B 2562/0247* (2013.01); *A61B 2562/0266* (2013.01); *G02B 6/262* (2013.01)

(56) References Cited

U.S. PATENT DOCUMENTS

| | | | |
|---|---|---|---|
| 9,587,976 B2* | 3/2017 | Wang | G01N 29/2418 |
| 2005/0062979 A1 | 3/2005 | Zhu et al. | |
| 2007/0083120 A1 | 4/2007 | Cain et al. | |
| 2008/0006763 A1* | 1/2008 | Vosburgh | G01L 1/242 |
| | | | 250/205 |
| 2008/0159687 A1 | 7/2008 | Donlagic et al. | |
| 2008/0319356 A1 | 12/2008 | Cain et al. | |
| 2009/0202195 A1* | 8/2009 | Lagakos | G01D 5/268 |
| | | | 385/13 |
| 2010/0069797 A1 | 3/2010 | Cain et al. | |
| 2011/0305118 A1 | 12/2011 | Daryoush et al. | |
| 2012/0010541 A1 | 1/2012 | Cain et al. | |
| 2014/0133280 A1 | 5/2014 | Daryoush et al. | |

OTHER PUBLICATIONS

C. Mu et al, "Broadband Fiber Optic Ultrasound Hydrophone Probe" 2004, Publisher: IEEE, pp. 149-152.

Gopinath et al., "Broadband Fiber Optic Hydrophone Sensors for Sub-Millimeter Ultrasound Resolutions", International Topical Meeting on Microwave Photonics, 2008, Jointly held with the 2008 asia-pacific microwave photonics conference, Mwp/apmp 2008, Sep. 9-Oct. 3, 2008, 4 pages.

Gopinath et al., "Improved Fiber Optic Hydrophone Sensors", IEEE, Ultrasonics Symposium, Oct. 28-31, 2007, 4 pages.

Gopinath et al., "Optimization of 100 MHz Fiber Optic Hydrophone for Medical Ultrasound Applications Using Nanometer Scale Gold Coating", Numerical Modeling of Medical Ultrasound, Acoustical Society Meetinq, Apr. 19-23, 2010, 39 paqes.

Minasamudram et al, "Thin Film Metal Coated Fiber Optic Hydrophone Probe", Applied Optics, Nov. 1, 2009, 48(31 ), G77-G82.

P.A. Lewin, et al, "Acousto-optic, point receiver hydrophone probe for operation up to 100 MHz" Jul. 5, 2005, Publisher: Science Direct, Ultrasonics 43, pp. 815-821.

\* cited by examiner

Taper angle, degrees

Cylindrically etched tip diameter, μm

FIBER OPTIC HYDROPHONE SENSORS AND USES THEREOF

STATEMENT OF GOVERNMENT INTERESTS

This invention was made with government support under Contract No. R01 EB007117 awarded by the National Institute of Health's NIBIB (National Institute of Biomedical Imaging and Bioengineering). The government has certain rights in the invention.

TECHNICAL FIELD

The disclosed inventions are in the field of devices for detecting acoustic pressure amplitude and phase for acousto-optic biomedical imaging.

BACKGROUND

Hydrophone devices can detect pressure amplitude in immersion media such as liquids or gases and in solids as well. Several different types of hydrophone devices are known in the art. New applications for sensing and use of pressure amplitude in liquids, solids and gases, including clinical, sonar, and communication applications require improved hydrophones for calibration, metrology, medical metrology, elasticity of medium, imaging, detection, therapy, diagnosis, and the like.

One type of hydrophone device known in the art is a piezoelectric hydrophone device. Piezoelectric hydrophones may be used for measurement of large frequency bandwidths; however, problems arise from the generation of high temperatures and cavitation effects that are produced by High Intensity Focused Ultrasound (HIFU) fields, High Intensity Therapeutic Ultrasound (HITU) fields, lithotripter fields or the like. These problems generally could lead to device failure due to high pressure amplitudes. Currently, such devices tend to be costly and cumbersome, and tend to have large apertures which can spatially average certain acoustic fields. For example, existing hydrophone probes have aperture diameters on the order of about 500 μm or more which introduces spatial averaging of acoustic fields beyond 3 MHz. This spatial averaging can lead to errors in detection and faithful reproduction of the pressure-time waveform of the measured acoustic wave and result in poor spatial resolution.

Other acoustic pressure sensors have been proposed as well, including a limited range of fiber optic based pressure sensors that exploits amplitude variations. There are at least two other broad classifications based on the sensing mechanism for these sensors, namely phase modulated and wavelength modulated pressure sensors. Included in phase modulated sensors are Mach-Zehnder interferometers, Fabry-Perot resonant structures and multilayer resonant structures that act as micro-interferometers. These interoferometric phase schemes however, are subject to the optical phase fluctuations which may result in higher amplitude noise of the sensor signal. Phase fluctuations, temperature drift and other problems associated with phase modulated fiber optic hydrophones can cause errors in acoustic pressure measurement.

Wavelength modulated phase sensors employing external Bragg's cells, fiber Bragg gratings (FBGs) and distributed Bragg reflectors have also been proposed. These fiber optic hydrophone devices perform acoustic sensing based on an acoustically induced change in the wavelength of optical signals passing through the given sensor. These wavelength modulated sensors are usually distributed along the length of the fiber and have sensing dimensions on the order of a few millimeters. The typical range for sensing regions in wavelength modulated sensors is on the order of about 600 μm to about 3 mm. This large sensing dimension causes the sensors to suffer from poor spatial resolution thus limiting the resolution bandwidth. For this reason, wavelength modulated fiber optic hydrophones cannot be used in many ultrasound applications.

Thus, what is needed is a novel, high sensitivity submicron resolution rugged hydrophone probe that would be able to characterize acoustic fields in the frequency range up to 100 MHz while minimizing spatial averaging, phase fluctuations, or both.

SUMMARY

Accordingly, the present invention provides for systems for detecting changes in pressure in an immersion medium such as a liquid, a gas, or a solid, the system comprising: an optical fiber, wherein the optical fiber has a core diameter at an immersion surface contact of the fiber of less than 10 μm; and a layer of material deposited on the side surface of the tip of the fiber as well as on the end face of the fiber tip, wherein the layer of material has a thickness of from about 2 nm to about 10 nm. Wherein the system is detecting changes in pressure in an immersion medium based on measuring changes in the intensity, phase, and/or wavelength in back reflected optical signal. In another embodiment, the fiber may have a diameter of less than about 20 um, and the diameter may be selected based on the frequency of the ultra sound.

The present invention also provides for methods for detecting changes in pressure in an immersion medium, such as a liquid or gas, or in a solid (collectively media or medium), the method comprising: contacting the medium with a fiber optic, wherein the fiber optic integrated with a light source and a detector, and wherein the fiber optic has a diameter of less than 10 μm at an immersion surface contact of the fiber; providing a thin layer of material on the immersion surface contact, wherein the thin layer of material is of a thickness in a range of from about 2 nm to about 10 nm; and detecting Fresnel back reflections from the immersion end of the fiber.

Also provided are methods of making a device for detecting acoustic waves in an immersion medium such as a liquid, gas, or solid, comprising: providing an optical fiber having a core diameter at an immersion surface contact of less than about 10 μm; and depositing on the immersion contact surface of the fiber a layer of material having a thickness of from about 2 nm to about 10 nm, and wherein detecting the pressure in the immersion medium is based on the direct interaction between evanescent electromagnetic fields exist outside the fiber tip surface and the ultrasound waves propagating in the immersion medium as well as detecting Fresnel back reflections from the immersion end of the fiber.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIGS. 4(a)-(b) depict a fiber with a straight cleaved immersion end, FIGS. 4 (c)-(d) depict a fiber with a cylindrically etched immersion end.

DETAILED DESCRIPTION OF ILLUSTRATIVE EMBODIMENTS

Figure 1:
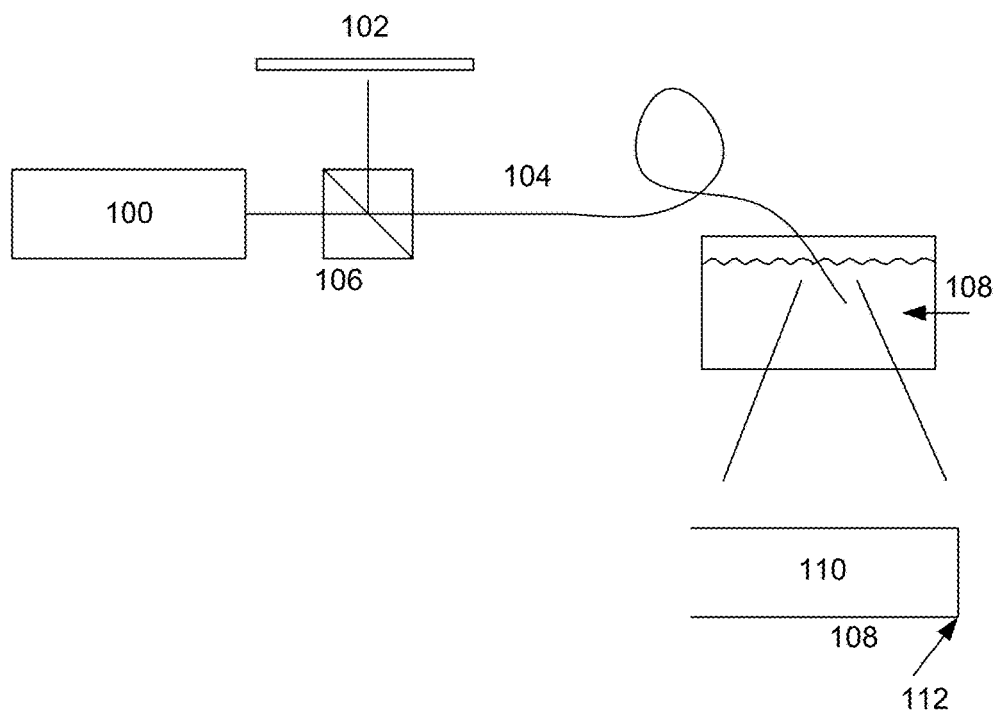
FIG. 1 depicts an example of a prior art fiber optic hydrophone.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As used herein, an immersion medium is any liquid, solid or gas capable of transmitting acoustic waves. An immersion end of the fiber optic hydrophone is the end of the fiber used in Fresnel back reflection mode and the immersion surface contact is the tip of the immersion end of the fiber having Fresnel back reflections associated therewith.

In an embodiment, an intensity modulated fiber optic hydrophone operating in a Fresnel reflective mode is provided with a fiber having a diameter at the immersion end of the fiber of under about 10 μm in order to characterize a frequency range of from about 0.5 MHz to about 500 MHz, where, as a specific example, a frequency range of up to about 100 MHz would require a fiber immersion surface contact diameter of about 7 μm for sampling at 100 MHz without introducing spatial averaging. It is possible that the diameter of the fiber would be less than 20 um, or even less than 30 um, and that the diameter may depend on the frequency of the signal being measured. The immersion end of the fiber may be provided with a thin layer of material having a thickness of from about 2 nm to about 12 nm on the immersion surface contact of the fiber and may also have an associated geometry, such as, for example, tapering, cleaving, or etching. As an example, the fiber optic hydrophones disclosed herein can be configured to measure the pressure versus time (p-t) waveform of the ultrasound field. These measurements may be used in one or more ways, such as, for example, for calibration of ultrasound devices, as a reference for ultrasound devices during use of the ultrasound device, metrology, medical metrology, determination of complex sensitivity vs. frequency, imaging, detection, sonar, diagnosis, communications, therapy and the like. Such devices may be optimized for sensitivity based on specific wavelengths, geometries, indexes of refraction, composition, diameters, plasmon excitation frequencies, and the like, for the selected thin layer materials.

In an example embodiment, a light source, a detector, and a thin layer of material can be provided. Light from the light source may be transmitted through the fiber. The thin layer of material is deposited on the immersion surface contact of the fiber, wherein the immersion end of the fiber is contacted with an immersion material, wherein the immersion material is any gas, liquid or solid. The immersion surface contact may thusly be contacted with the liquid, solid or gas. The detector may detect Fresnel back reflections due to the change in index of refraction between the immersion contact surface of the fiber, the thin layer of material and the immersion material, or solid. Changes in pressure may cause the complex index of refraction of the immersion material or solid to change, or it may place strain on the immersion material, as it may also cause the complex index of refraction of the thin layer of material to change due to strain. The changes in index cause a change in the Fresnel back reflections. The detector detects these changes in Fresnel reflections and correlates them with the change in index of refraction. Pressure measurements of the immersion medium or solid may then be determined. In an embodiment, light from the source passes through the fiber, is reflected from the end of the fiber by the thin film of dielectric material and is detected by a detector. Variations in the amount of reflected light may be used to determine the pressure acting on the thin film, which may be proportionate to the pressure acting on the immersion material or solid material.

In a configuration of the example embodiment mentioned above, the thickness of the thin film may be in the range of from about 1 nm to about 30 nm. Early research in these thin films predicted that a decrease in the thickness of a thin film below 30 nm would not yield an increase in the sensitivity. This view was due in part to the perception that the thin layer was over an order of magnitude thinner than the wavelength of light (1550 nm wavelength with a 50 nm layer of material), so no great variation in sensitivity was expected. Surprisingly, however, new increases in sensitivity and sensitivity maxima were found by decreasing the layer thickness. For example, in one configuration, the thickness of the film may be in the range of from about 1.5 nm to about 25 nm. In another configuration, the thickness of the film may be in the range of from about 2 nm to about 20 nm. In a further configuration, the thickness of the film may be in the range of from about 2.5 nm to about 15 nm. In another configuration, the thickness of the film can be in the range of from about 3 nm to about 10 nm, or even in the range of from about 3.5 nm to about 8 nm.

In an example embodiment, the optimum thickness of the thin film may be determined based on the optimum back reflectance equation:

a. $\frac{\partial R}{\partial p} = \frac{\partial R}{\partial n_c}\frac{\partial n_c}{\partial p} + \frac{\partial R}{\partial n_w}\frac{\partial n_w}{\partial p} + \frac{\partial R}{\partial n_g}\frac{\partial n_g}{\partial p} + j\frac{\partial R}{\partial k_g}\frac{\partial k_g}{\partial p}$ b. where $R = \Gamma_{in}\Gamma_{in}*$ and $\Gamma_{in} = \frac{n_d(n_c - n_w) + (n_w n_c - n_d^2)\tanh\gamma d}{n_d(n_c + n_w) + (n_w n_c + n_d^2)\tanh\gamma d}$ In such an embodiment, several factors may be influential, such as, for example, $$Y = j\left(\frac{2\pi(n - j.k)}{\lambda}\right),$$

where $\lambda$ the wavelength of the laser, the index of refraction of the fiber ($n_c$), the geometry of the fiber, the index of the immersion material ($n_w$), and the type of material of the thin layer ($n_d$). The optimum change in compression of thin layer due to pressure may be described as $$\frac{\partial R}{\partial p} = \frac{\partial R}{\partial d}\frac{\partial d}{\partial p}.$$

Optimum slope value of reflectance and pressure is achieved in optimum change in complex index of refraction for the coating layer due to pressure. When the plasmon excitation frequency of the thin layer of material given in the following equation matches with particular light source wavelength, then an increase in complex index is observed and the like may be considered in determining a desired thickness of the thin layer of material.

$$\left(\text{Re}[\varepsilon(\omega)] = 1 - \frac{\omega_p^2}{\omega^2},\right.$$

Where, $\varepsilon(\omega)$ is the complex permittivity of the thin film, $\omega_p$ is the surface plasmon resonance frequency.

In an embodiment, a fiber optic hydrophone disclosed herein operates in the reflective mode based on the principle of intensity modulation in Fresnel reflectance from the immersion surface contact of an optical fiber. The fiber can be immersed in, or placed in contact with an immersion medium or solid, where an immersion medium can be any gas, liquid, or solid. Acoustic waves acting on the immersion medium may cause a change in the index of refraction of the immersion medium, which in turn would cause a change in the Fresnel reflectance. Moreover, measurements in the change of Fresnel back reflectance may also be correlated with changes in pressure at the immersed end. Other aspects of the principle and use of reflective fiber optic hydrophones will be well known to one having ordinary skill in the art.

In an embodiment, an addition of a thin layer of material on the immersion surface contact of a fiber sensor can provide an improvement in sensitivity over the sensitivity of an uncoated fiber. Initial exploration of this phenomena using transmission line models and other analytical methods provided an estimate of ideal thickness on the order of over about 30 nm. Surprisingly, however, improved models, testing, and methods have shown that there is a further increase in sensitivity using thinner layers than previously suggested. In fact, using the previously known models, any decrease from a 30 nm coating layer would not have provided any increase in the sensitivity of the hydrophone. New experiments and analysis have shown, however that there is a surprising increase in sensitivity with even thinner layers of material.

In another embodiment, a wavelength of a light source or laser, the taper angle of the immersion end of the fiber, the core and cladding diameter, taper length, fiber index, thin layer material, thin layer thickness and other fiber geometries may be varied in order to change, and in some circumstances to increase the sensitivity of the fiber optic hydrophone. As an example, the factors listed above may be adapted to optimize the sensitivity of a fiber in a particular circumstance and for a particular use. In another embodiment, the plasmon excitation frequency of the material selected for use as the thin layer material may be considered in determining the ideal thickness of the layer. For example, the plasmon resonance frequency for a given material at a given wavelength may be used to determine the optimal thickness for the thin layer. As a further example, a method of manufacture of these materials may optimize a fiber optic hydrophone by varying the above noted elements for a particular use or a range of uses. These uses may include, without limitation, metrology, medical metrology, determination of elasticity, of ultrasound or other acoustic devices, calibration of medical instruments, diagnosis, therapy, other medical uses, sonar, communications and the like.

FIG. 1 is a depiction for the setup of a previously known fiber optic hydrophone that operates in a reflective mode. In FIG. 1, there is a light source 100 which provides light to a fiber 104, where the fiber has a diameter at the immersion surface contact of greater than 15 µm. Light passes through the fiber which has one end of the fiber 110 immersed in a medium or contacted with a solid 108. Some portion of the light from the source 100 can be reflected from the fiber/medium interface 112, which can be transported back through the fiber 104, split off by beam splitter 106 and detected by detector 102. Variations in pressure in the immersion medium or solid 108 can cause changes in the index of reflection of the immersion medium or solid, 108, which can in turn cause a change in the amount of light reflected back to detector 102. Thus, a measurement of pressure may be made based on the amount of light received by detector 102.

Figure 2:
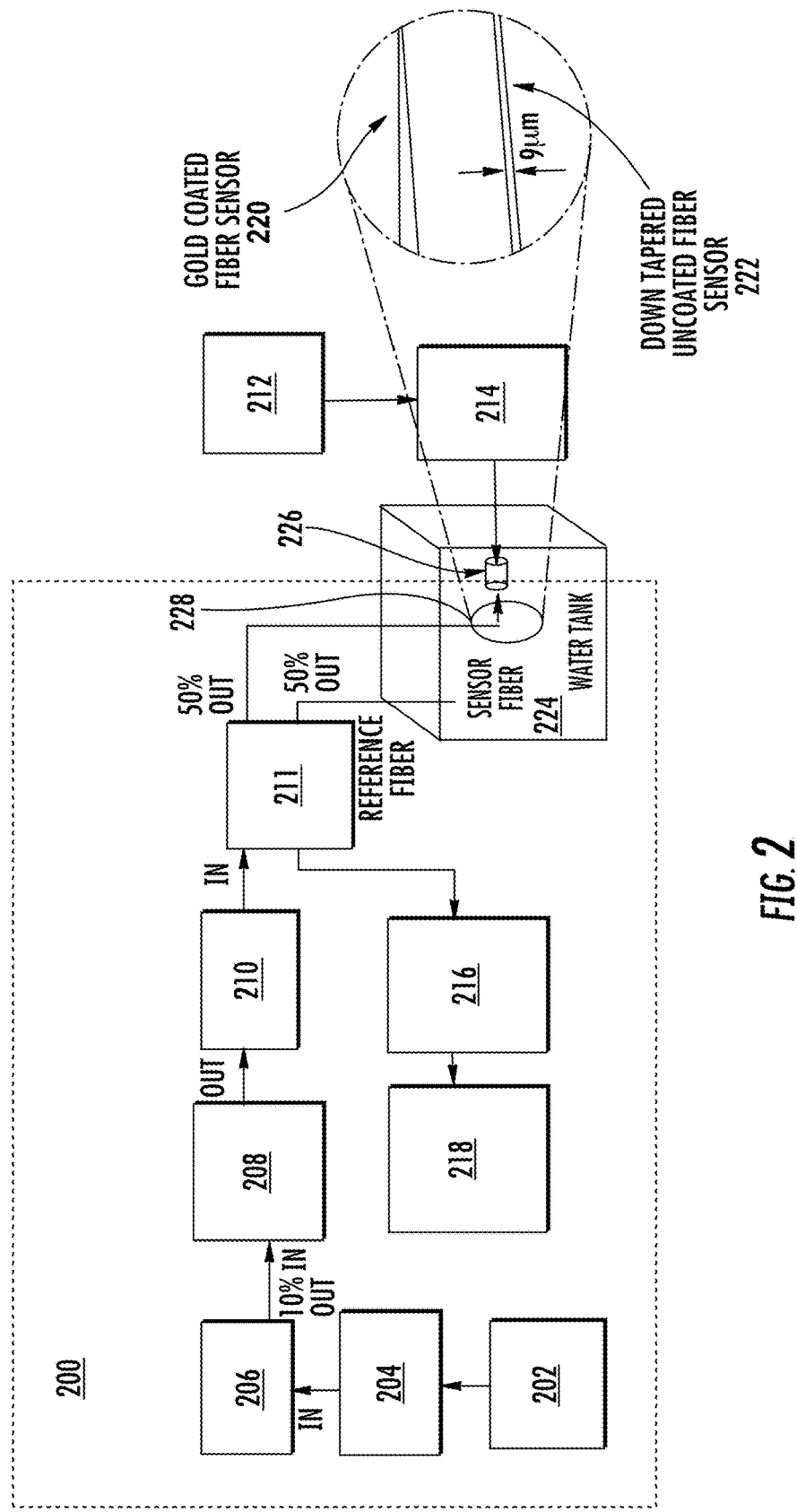
FIG. 2 depicts an example embodiment of an experimental setup of the present invention.

FIG. 2 depicts a non-limiting experimental setup of an example embodiment of the present invention. One having ordinary skill in the art would understand that certain elements of the diagram are not necessary to the operation of the fiber optic hydrophone, that any number of elements may be added to the setup and that the fiber optic hydrophone can vary in a number of ways, including ordering of specific elements, from the experimental setup disclosed in FIG. 2.

A fiber optic hydrophone may comprise a light source 202. The light source depicted in FIG. 2 may be any light source capable of providing light to a fiber and a Fresnel back reflection from the interface between the immersion end of the fiber and the immersion material or solid. In one embodiment, the light source 202 may be any type of laser, distributed feedback laser, pulsed laser, continuous wave laser, light emitting diode with a narrowband optical filter, bulb, lamp, or the like with a narrowband optical filter. In a series of non-limiting example embodiments, the light source may be one or more lasers or LEDs followed with a narrowband optical filter with an output anywhere in the range of about 300 nm to about 2500 nm, or, as a series of non-limiting examples, sources having wavelengths in the range of from about 450 nm to about 900 nm, or in the range of from about 900 nm to about 1300 nm, or of from about 1300 nm to about 1700 nm. The light source may also emit radiation at about 1620 nm, 1550 nm, 1410 nm, 1060 nm, 980 nm, 850 nm, 830 nm, 800 nm, 780 nm, 680 nm, or 633 nm. The light source emits light that is coupled into the fiber optic 228 for Fresnel back reflections that may be detected by the detector 216 as shown above with respect to FIG. 2. The light source may be polarized, or it may be unpolarized.

In an embodiment depicted in FIG. 2, a fiber optic hydrophone may comprise one or more of optical isolators 204 and 210, optical couplers, 206 and 211, and optical amplifiers such as 208. As a series of example embodiments, an optical amplifier can be an Erbium doped fiber amplifier, or semiconductor optical amplifier, Raman amplifier, as another example, any optical amplifiers may be selected such that they amplify within a range of emission from light source 202. Further, the isolators 204 and 210 and couplers 206 and 211 may also be selected such that they isolate and couple one or more wavelengths of light within a range of emission from light source 202. While FIG. 2 depicts couplers, amplifier and isolators, there is no requirement that a fiber optic hydrophone have any of these elements, though a fiber optic hydrophone may have one or more of any of the above.

In an embodiment, a signal generator 212, power amplifier 214, and ultrasound generator 226 may provide a signal for an output that may be captured by the immersion end of fiber optic 228. While the figure depicts an experimental setup, wherein the signal generator 212, power amplifier 214, and ultrasound generator 226 are used to test the sensitivity and durability of fiber optic hydrophone 200, in another embodiment, a signal generator and amplifier may be configured to transmit through, or reflect pressure amplitude off of, one or more surfaces. Transmissions or reflections off of these surfaces could be used by one or more fiber optic hydrophones to determine aspects of the surfaces. As an example, signal generator 212, power amplifier 214, and ultrasound generator 226 could be used to provide a signal which could reflect off of one or more organs of a patient. These reflected signals could be detected by an array of fiber optic hydrophones such as fiber optic hydrophone 200 to image the organs, cells, tissue and the like. It should be noted that while reflecting signals off of surfaces is one way to image surfaces, this is not intended to be a limiting example, and one or more fiber optic hydrophones could be used to image surfaces in any manner known in the art.

As another example, a communications system may be created using the fiber optics hydrophones disclosed herein. For example, in a naval vessel or army tank having a closed compartment where it is desirous not to have wires entering or exiting the compartment, pressure amplitude with a high frequency bandwidth may be transmitted by one or more signal generators and detected by a fiber optic hydrophone after the signal passes through a structure. The high bandwidth possibilities in a range of up to about 200 MHz may be detected without error and such high bandwidth may provide high speed communications. Further, an array of fiber optic hydrophones could be used in other configurations to determine the wavefront of an acoustic wave over an area.

Signal generator 212, power amplifier 214, and ultrasound generator 226 show one way to create acoustic signals for imaging or communications or the like. Any other type of acoustic signal generator may also be used including one or more of naturally occurring, mechanical, or electric signal generators.

FIG. 2 depicts a detector 216 and a spectrum analyzer 218. The detector 216 may be any detector known in the art capable of detecting electromagnetic radiation. In one embodiment, an avalanche photodiode, a PIN photodetector, Schottky photodiode may be used. In another embodiment, an MSM, a CCD, or a APD detector is used. Any other detector may be selected based on sensitivity requirements and the wavelength and/or wavelengths of light emitted from the light source and transmitted through the fiber. The detector 216 can detect changes in Fresnel back reflections from the immersion end of fiber optic 228.

FIG. 2 depicts a water tank 224. The water tank was used as an experimental set-up, however, the fiber may be immersed in any immersion material or contacted with a solid. As an example, water tank 224 could represent an individual, wherein the fiber optic hydrophone 200 is used in vivo during an operation. As another example, the fiber optic hydrophone could be placed on a surface, such as with or without gel on skin of a patient or animal. As another embodiment, a medium could be placed in contact with an item of interest and fiber optic hydrophone 200 can be placed in the gas or fluid such that it may determine aspects of the pressure amplitude of the item. As a further example, the immersion material could be any gas, or any liquid, such as, for example, air or salt water.

FIG. 2 depicts examples of two immersion ends of fiber optic 228. Immersion end 222 an uncoated tapered fiber and 220 is tapered fiber with a layer of gold on the immersion surface contact of the fiber optic. In the experimental setup of FIG. 2, each fiber has a tapered end and there is an uncoated end on one of the fibers. These are non-limiting embodiments of the immersion end of the fiber. In another embodiment, the immersion end of the fiber comprises an untapered end and a thin layer of material on the immersion contact surface of the fiber. As another embodiment, the immersion end of the fiber may comprise a tapered end and an angle cleaved immersion contact surface coated with a layer of material. The taper angle, cleave angle, and taper length may vary in any way known in the art. These aspects of the immersion end of the fiber may be selected such that the sensitivity of the fiber optic hydrophone is maximized for a particular use or for a range of uses.

In an embodiment, the fiber optic 228 of FIG. 2 can be selected such that it will transmit light emitted by light source 202 depicted with respect to FIG. 2. This does not mean to imply that the fiber may only be selected based on the light source, or that the fiber must be optimized for transmission of the light source, however, in one embodiment, fibers optimized for light source outputs 202 may be used in the fiber optic hydrophone. In a further embodiment, the index of refraction of the fiber optic is provided and may be used in one or more ways to determine thicknesses of the thin layer of material as depicted above with respect to FIG. 2. For example, the intensity of a Fresnel reflection may be varied based on the index of refraction of the fiber.

In an embodiment, the fiber 228 may be a single mode fiber and may have a core diameter at the immersion surface contact of less than about 20 um, 15 µm, or even less than about 10 µm. As a further example, the core diameter at the immersion surface contact may be in the range of from about 2.5 µm to about 12 µm, or in the range of from about 4 µm to about 10 µm, or even in the range of from about 4.5 µm to about 8 µm. Fibers having diameters at the immersion surface contact in the range above may have tapered ends, where the taper terminates with a fiber having core diameters in the above noted ranges. These fibers may also be etched where the diameter of the core terminates at the immersion surface contact with a diameter in any of the ranges noted above. In one embodiment, the fibers may have cylindrical cores or elliptical cores or any other core geometry known in the art.

In one embodiment, selection of the diameter of the fiber is determined based on the frequency range of interest. For example, the active sensor aperture size, or fiber core diameter at the immersion surface contact may be selected such that it is comparable with the half acoustic wavelength at the highest frequency of interest. In such an example, in order to eliminate the effects of spatial averaging, a hydrophone may sample a field with at least half-wavelength resolution in a range of from about at least 70 MHz, to about 500 MHz, where, as an example, sampling a field with at least half-wavelength resolution of 100 MHz in water would require an active sensor aperture size on the order of about 7 µm. In other embodiments, the field of sampling may be up to about 500 MHz with a much smaller fiber aperture. Based on these aperture size requirements, single mode fibers may be selected for fiber optic hydrophones. The fiber 228 used in the fiber optic hydrophones described herein may be any one of the fibers available for sale, or any other fibers known in the art.

As one example, the core of the fiber 228 should be selected such that it approximates a point source for detection and is thus capable of receiving a large bandwidth of acoustic information. As noted above, several prior art technologies lacked the capability to appropriately measure pressure amplitude without error due to spatial problems. Limiting the diameter of the core of the fiber to a single mode with a narrow diameter may provide a reduction in the spatial errors of the system.

Other elements may be included in the system. For example, in one embodiment the system may further comprise one or more of optical isolators, couplers, filters, positioners, lenses, polarizers, wave plates, mirrors, transducers, spectrum analyzers, additional lasers, amplifiers, signal analyzers and generators, power sources, detectors, fibers, positioning elements such as stands, mounts, robotic arms and the like.

In addition, one or more computing elements may be associated with one or more of the elements depicted in FIG. 2 and may provide input to those elements and receive output. Computing elements may also perform calculations based on received input. For example, data output from the detector and data output from the light source may be used to calculate or otherwise determine changes in pressure. In addition, any other element depicted in FIG. 2 or described above may be configured to work in conjunction with computing elements and may have associated therewith, output and input. These connections to one or more computing elements may be wired or wireless.

In one embodiment, the thin layer of material on the immersion surface contact of fiber 228 may comprise gold. Other metallic materials may also be used as the layer at the immersion surface contact of the fiber. As non-limiting examples, the layer may comprise one or more of Ag, Au, Pt, Al, Co, Ni, Ti, Ga, In, Cr, Mo, any other metal and/or any metallic alloy. Plasmon resonance frequencies of metallic materials having large change in complex index of refraction properties during stress may be used to select a material. A metal or combination of metal materials may be used to form the thin layer of material on the immersion surface contact of the fiber. In another embodiment, multiple layers may be provided on the immersion surface contact of the fiber. As one example, the strain properties of a metal can be related to change of index of refraction of the metal. Knowledge of the plasmon excitation frequency, the reflectance and the strain properties of a metallic material or, in another embodiment, a dielectric material may be used to optimize the sensitivity of a fiber optic hydrophone at a given wavelength for a given application or range of applications.

In an embodiment, the thickness of the thin layer of material may be selected based on the plasmon excitation resonance frequency of the material for a given wavelength of light. Correlating the wavelength with the plasmon excitation frequency may provide an optimal thickness. As one example, the formula for selecting thickness based on these factors may be maximizing back reflectance change due to thickness variation and large change in thickness due to stress such as $$\frac{\partial R}{\partial p} = \frac{\partial R}{\partial d}\frac{\partial d}{\partial p}.$$

In another embodiment, one or more dielectrics may be used as the thin layer of material on the immersion surface contact of the fiber. For example, TiO2, may be used individually or in combination with any of the other metals and/or an dielectric material. As one example, the strain properties of a material can be related to change of index of refraction of a material due to strain. Knowledge of the reflectance and strain properties of a metallic material or dielectric material may be used to optimize the sensitivity of a fiber optic hydrophone for a given application or range of applications.

The thin layer of material described above may be coated on the immersion surface contact of the fiber using any method known in the art. As one example, a thin material such as, for example gold may be coated using one or more of sputtering techniques, molecular beam epitaxy, metaorganic chemical vapor deposition, evaporation techniques, wet or dry chemistry techniques, or any other film growth or coating technique. In one embodiment, the fiber optic hydrophones disclosed herein may be placed in harsh environments, that is, environments having very high levels of pressure amplitude. Other known hydrophones may have failed, for example, near or in the focal zones or volumes of High Intensity Focused Ultrasound (HIFU) fields, High Intensity Therapeutic Ultrasound (HITU) fields, or in Lithotripsy calibration. In one embodiment, the fiber optic hydrophone disclosed herein may be particularly suited to measurement of these high levels of pressure amplitude because a failure mode is peeling off the thin layer of material on the tip of the fiber. In such an example, one or more of the above mentioned layer growth or deposition methods may provide increased adhesion.

In an embodiment, the thickness of the layers can be selected such that they are optimized for sensitivity to pressure. As used herein, sensitivity to pressure may comprise the ratio of change in index of refraction of the layer to a change in pressure of the immersion medium or solid. In one embodiment, the more a layer changes index of refraction as changes in pressure in an immersion medium or solid, the more sensitive it is. As an example of the above, changes in index of refraction may cause changes in the amount of light received at the detector, which may thus be proportional to the change in pressure of the immersion medium or solid.

Figure 3:
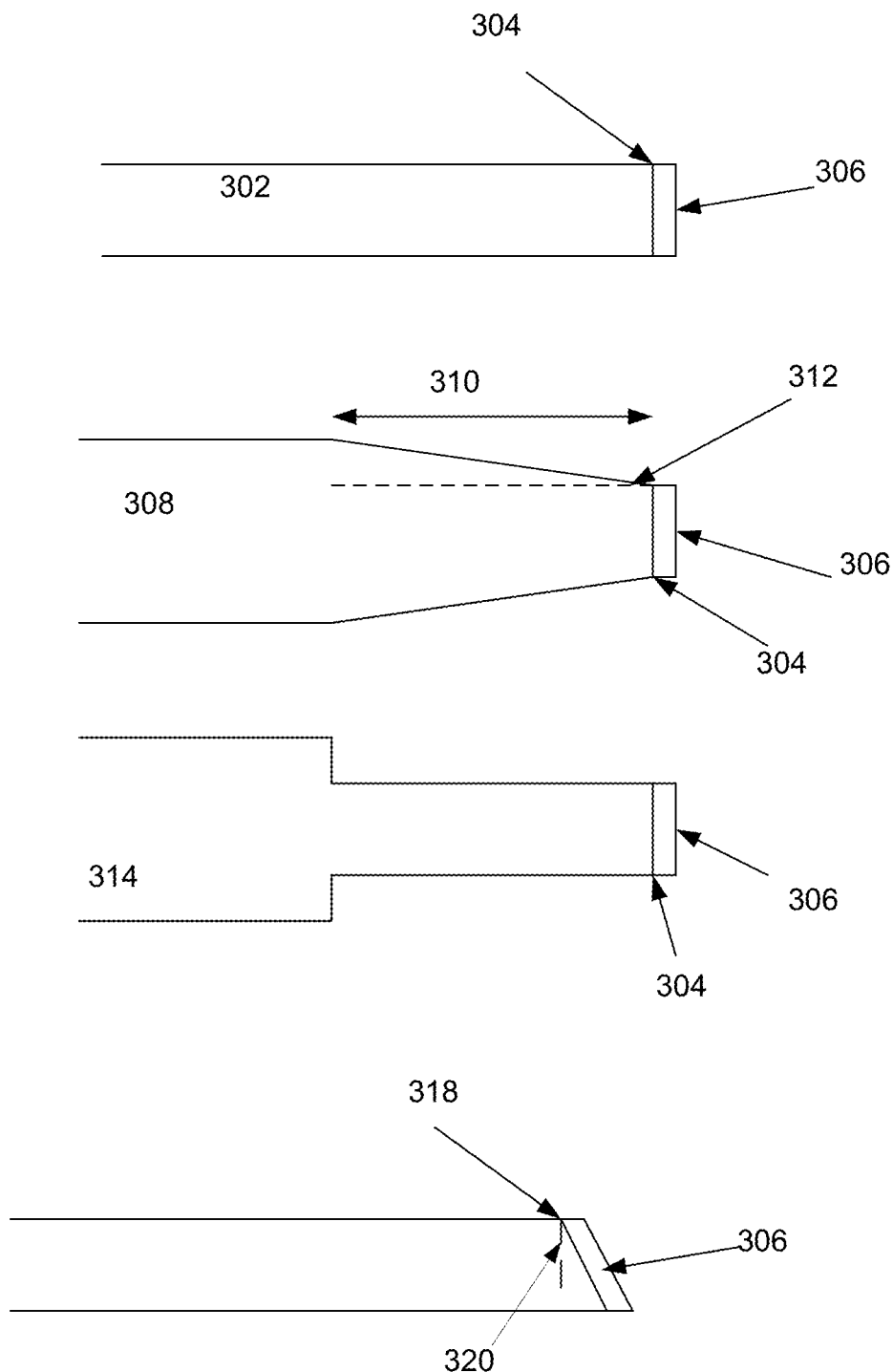
FIG. 3 depicts examples of fiber optic hydrophone immersion surface contact geometries.

FIG. 3 depicts a series of immersion ends of a fiber optic hydrophone, where the immersion ends are those ends immersed in a medium, or contacted with a solid. In one embodiment, when an immersion end of a fiber is immersed in an immersion medium or contacted with a solid and it may detect pressure amplitude and changes in pressure. As noted above, a fiber may be a straight cleaved fiber 302 where there is no etching or tapering of the fiber. The straight cleaved fiber will have an immersion surface contact 304 and, in one embodiment, comprise a thin layer of material 306.

In an embodiment, the immersion end of a fiber optic hydrophone may also be a tapered immersion end 308. The tapered fiber may have a taper length 310 and a taper angle 312. The taper may be linear, or it may be exponential or it may have any other suitable geometry such as parabolic or hyperbolic. The tapered fiber will have an immersion surface contact 304 and may comprise a thin layer of material 306.

In an embodiment, the immersion end of a fiber optic hydrophone may also be an etched end 314. In one embodiment, this will be a cylindrical etch, while in another embodiment it may be an elliptical etch or have a different etching geometry. The immersion end of the fiber will have an immersion surface contact 302 and may comprise a thin layer of material 306.

In another embodiment, the immersion end of a fiber optic hydrophone may be an angle cleaved fiber 318. This cleave angle 320 may be any angle in a range of from about 0 degrees to about 45 degrees. The immersion contact surface of the angled cleave may comprise a thin layer of material 306.

FIGS. 4 (a)-(f) depict a series of images and modeled geometry for: (a) and (b) a straight cleaved uncoated fiber optic hydrophone; (c) and (d), a cylindrically etched fiber optic hydrophone and (e) and (f) a linearly tapered fiber optic hydrophone. Each of the sensors may comprise a thin layer of material on the end as noted above with respect to FIG. 2. As noted with respect to FIG. 4, the fiber may be cylindrical, or cylindrically etched. Further, the fiber may be tapered as shown with respect to FIG. 4(e). In one embodiment, the fibers may have cylindrical cores or elliptical cores, and may be either cylindrically etched or elliptically etched, or etched otherwise.

The tapering of the fiber may be linear, however, in another embodiment, the tapering may not be linear, but may instead be an exponential tapering or it may be tapered according to any other method known in the art, such as, for example, hyperbolic or parabolic or otherwise non-linear. As an example, the tapering angle may be in a range of between about 0 degrees and about 45 degrees. The tapering length on a fiber optic hydrophone may be any length known in the art and may comprise any length in a range of from about 10 μm to about 1 mm.

The selection of the tapering angle, tapering length and other geometries of the tip of the fiber may be selected in order to optimize the sensitivity of the fiber optic hydrophone. As shown below with respect to FIG. 7, in one experimental setup, the taper angle and geometry had an effect on the sensitivity. While the taper angle and taper length may be beneficial to the sensitivity of the fiber optic hydrophone in some embodiments, the above is not intended to imply that taper angles and lengths are necessary for any particular embodiment. Further, it should be noted that various aspects of a fiber optic hydrophone have relationships between them. For example, a straight cleaved, non-etched fiber at 980 nm require a thin layer of material at a first thickness in order to optimize the sensitivity of the fiber optic hydrophone. However, a tapered, etched fiber at 980 nm may require a thin layer of material at a different thickness in order to optimize the sensitivity of the fiber optic hydrophone.

Figure 4A:
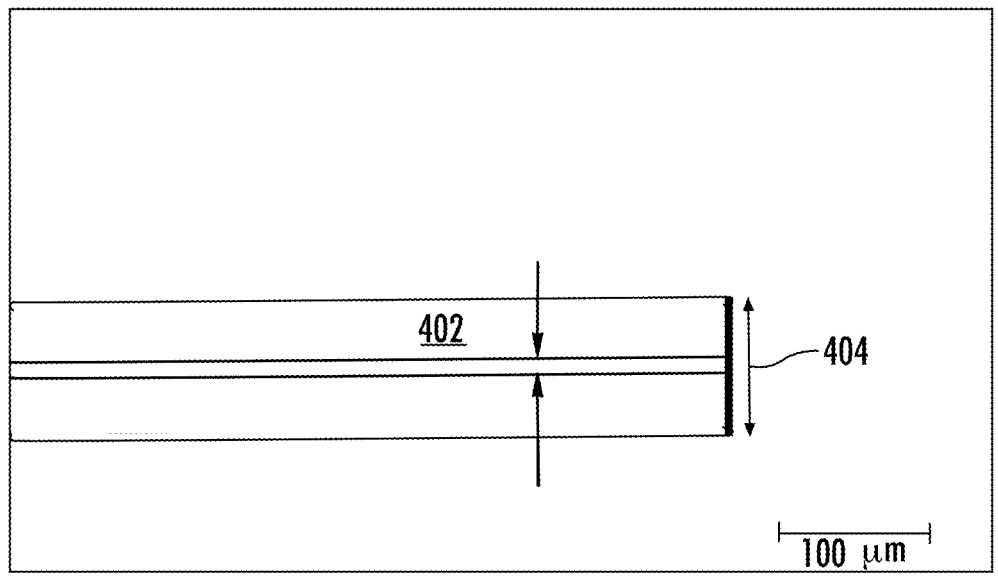
FIGS. 4(a), (b), (c), (d), (e) and (f) depict a series of immersion surface contacts and different associated geometries.
Figure 4B:
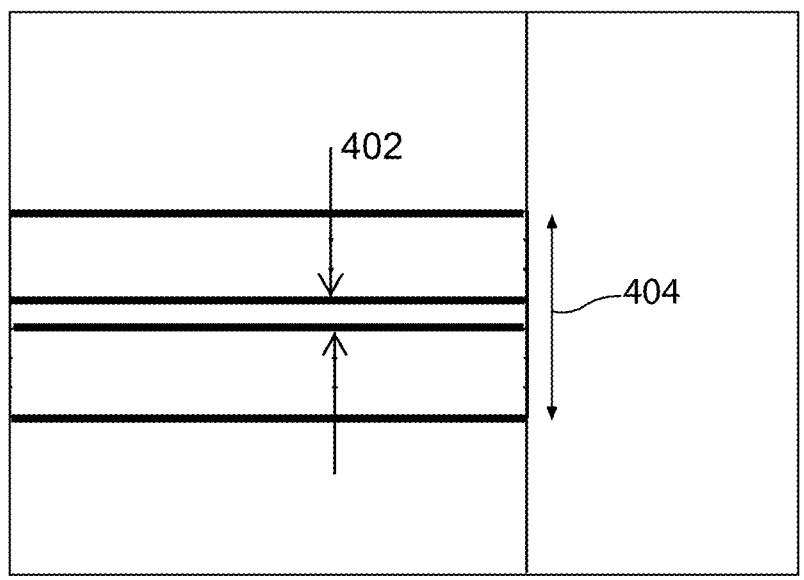
Figure 4C:
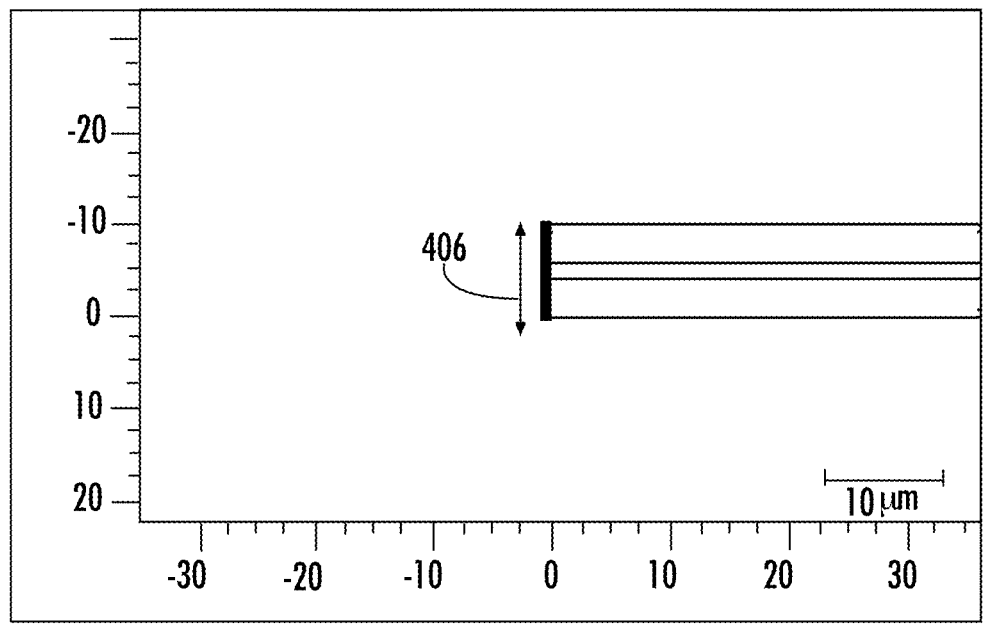
Figure 4D:
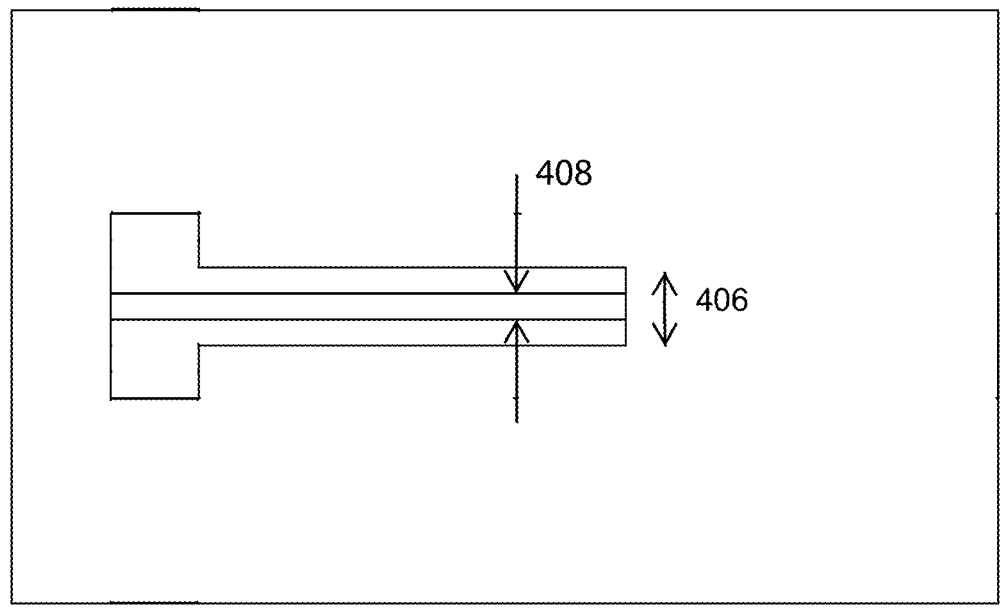
Figure 4E:
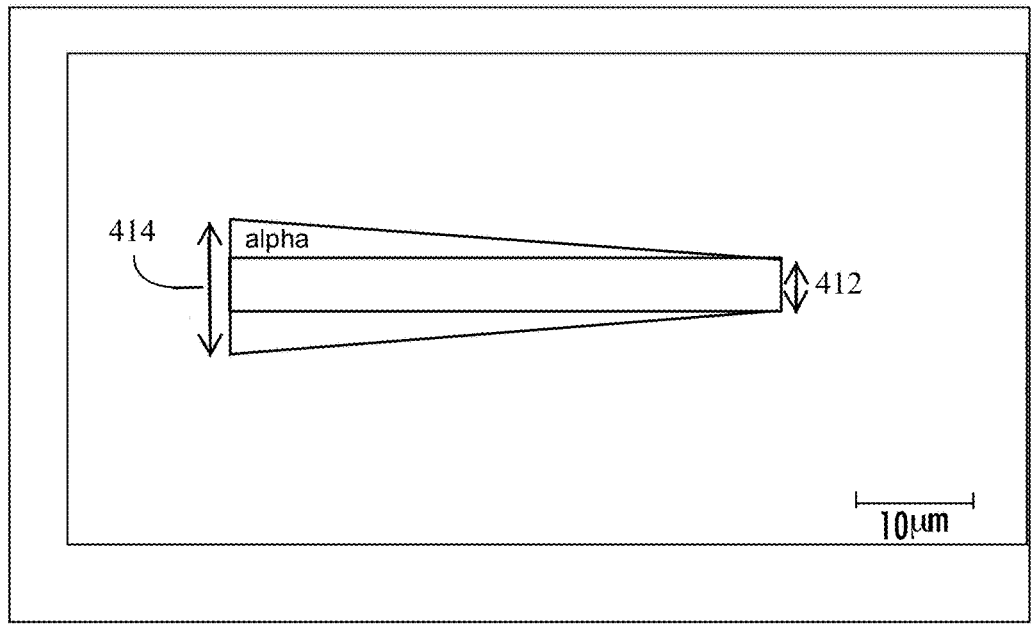
FIGS. 4(e)-(f) depict a fiber with a tapered immersion end.
Figure 4F:
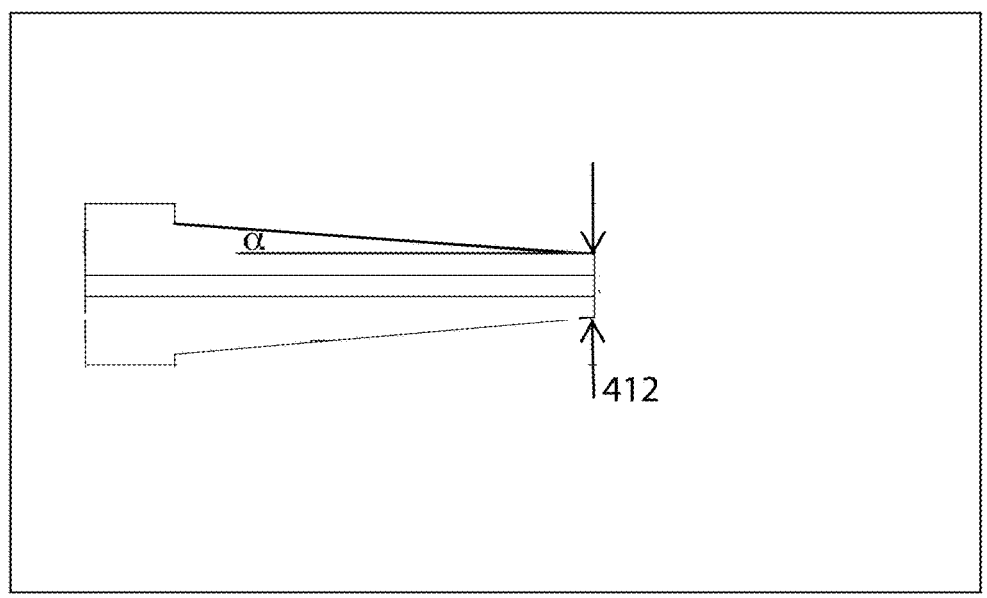

FIGS. 4(a) and (b) depict a fiber having a core diameter 402 and an un-etched cladding diameter 404. As noted above, the core diameter of the fiber may be selected such that it approximates a point source for detection and is thus capable of receiving a large bandwidth of acoustic information. As noted above, several prior art technologies lacked the capability to appropriately measure pressure amplitude without error due to spatial averaging problems. Limiting the diameter of the core of the fiber to a single mode with a narrow diameter may provide a reduction in the spatial averaging errors of the system. In an embodiment, the diameter of the fiber core is about 8 μm. Elements 406 and 408 depict the diameter of the cladding and core of an etched fiber, and 412 and 414 depict the diameter of a tapered fiber at opposite ends of the taper.

Figure 5:
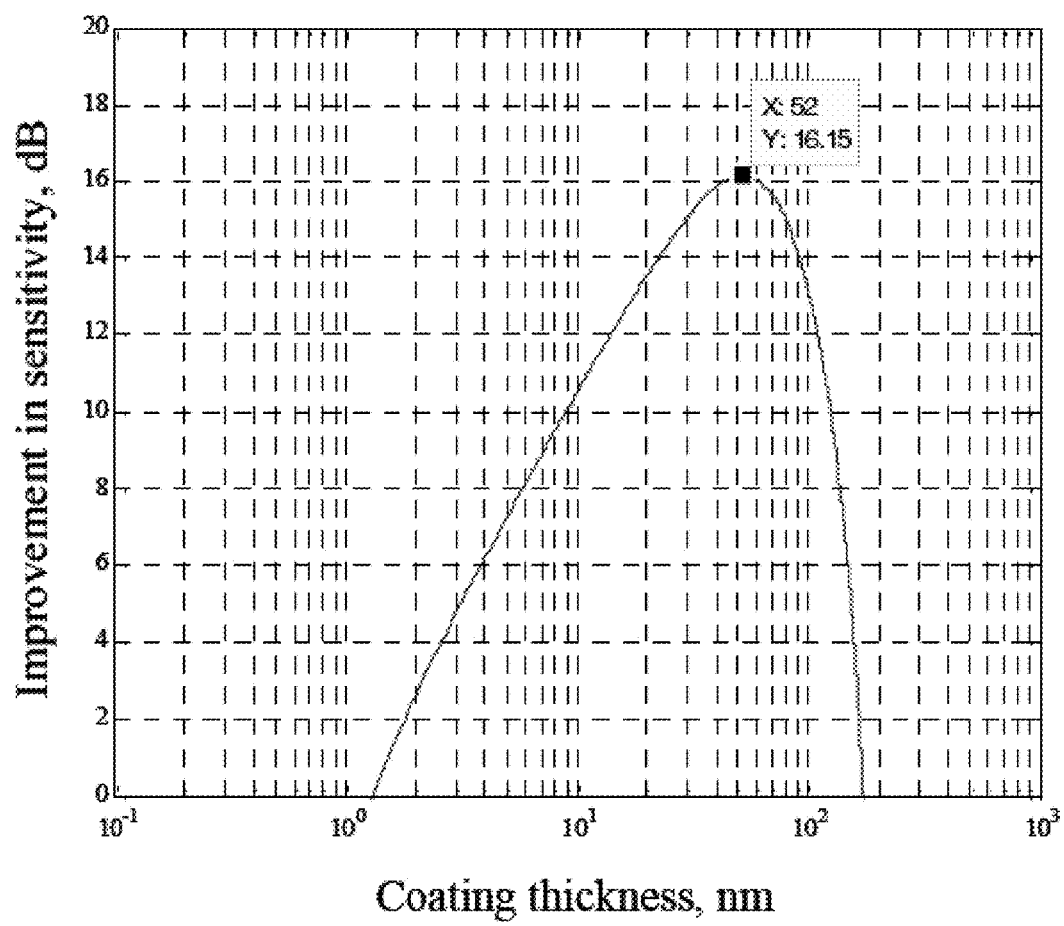
FIG. 5 depicts a previous model suggesting that there was no improvement in hydrophone sensitivity for gold coating thicknesses of less than about 30 nm.

FIG. 5 depicts a logarithmic graph with the expected results for a thin layer of gold placed on the immersion surface contact of a straight cleaved fiber optic hydrophone. For this graph, classical TEM line approaches of modeling were used and it can be seen that the optimal thickness was greater than 30 nm.

Figure 6:
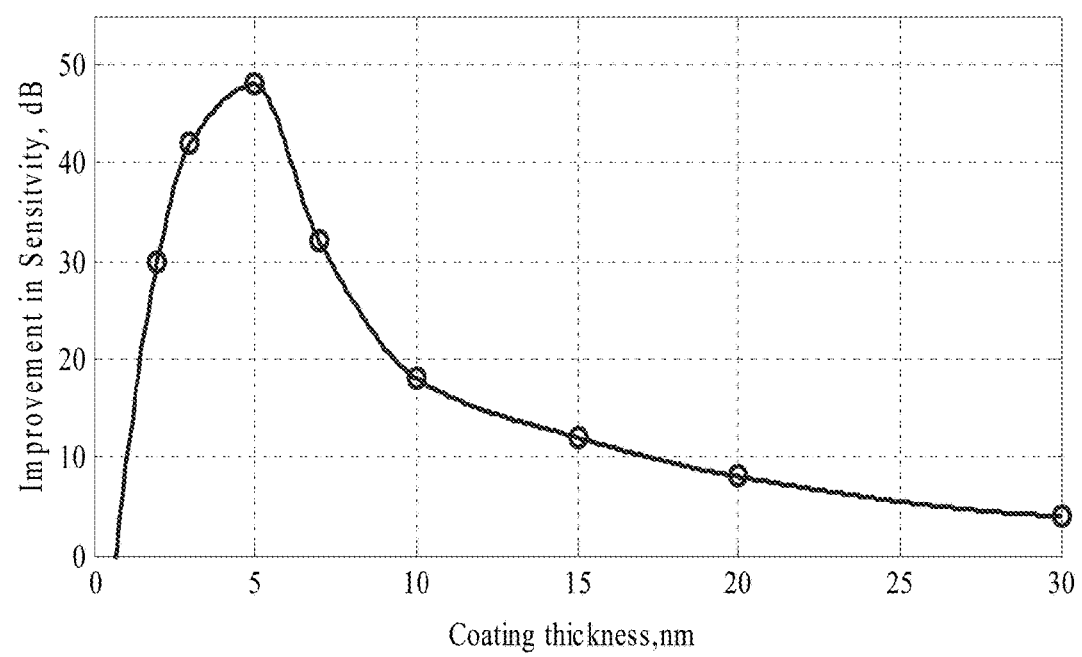
FIG. 6 depicts experimental results for sensitivity of a fiber optic hydrophone with thin layers of gold on the immersion end of the fiber.

FIG. 6 depicts a more accurate full-wave electromagnetic field modeling of the said structure with a surprisingly good experimental results in sensitivity of a fiber optic hydrophone at 1550 nm with a much thinner layer of gold coated on the immersion surface contact of the immersion end of a fiber. The diameter of the fiber in this example was reduced to about 6 μm, and the fiber was cylindrically etched. As is clear from comparing FIG. 5 and FIG. 6, there is a considerable difference in the improvement levels and the optimum gold coating thickness with an improvement peak expected using thinner gold coating material. FIG. 6 depicts a single set-up of a fiber optic hydrophone and is not meant to depict the optimal thickness of a thin layer on the immersion contact surface for all fiber optic hydrophones. As noted above, altering one or more aspects of the set-up, including the wavelength, thin layer material, complex index of refraction, optical fiber geometry, immersion material and geometry of the fiber can affect the optimal thickness.

Figure 7:
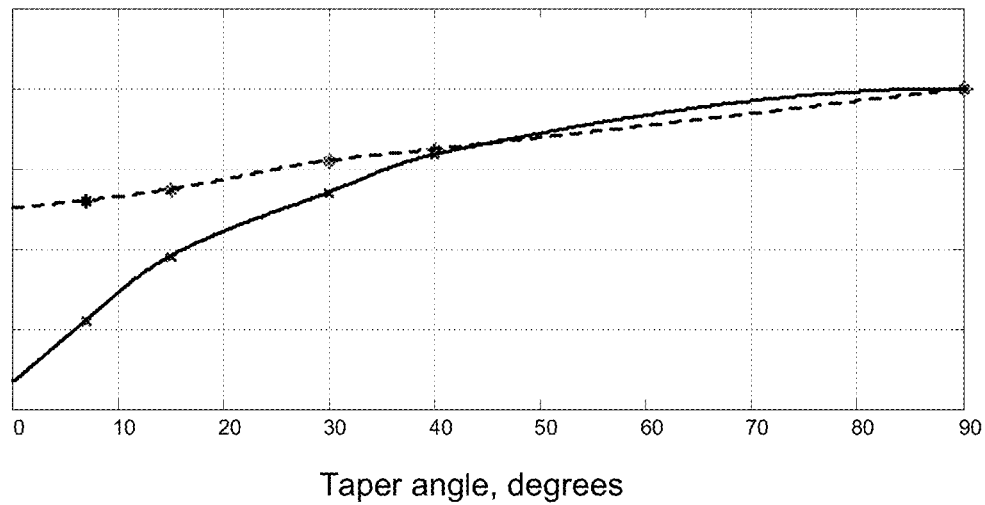
FIGS. 7(a) and (b) depict the sensitivity effects of core diameter in an example embodiment of a cylindrically etched fiber and the sensitivity effects of taper angle in an example embodiment. The units on the left side of the graph would show a relative improvement in sensitivity in dB and exists as an example.
Figure 7:
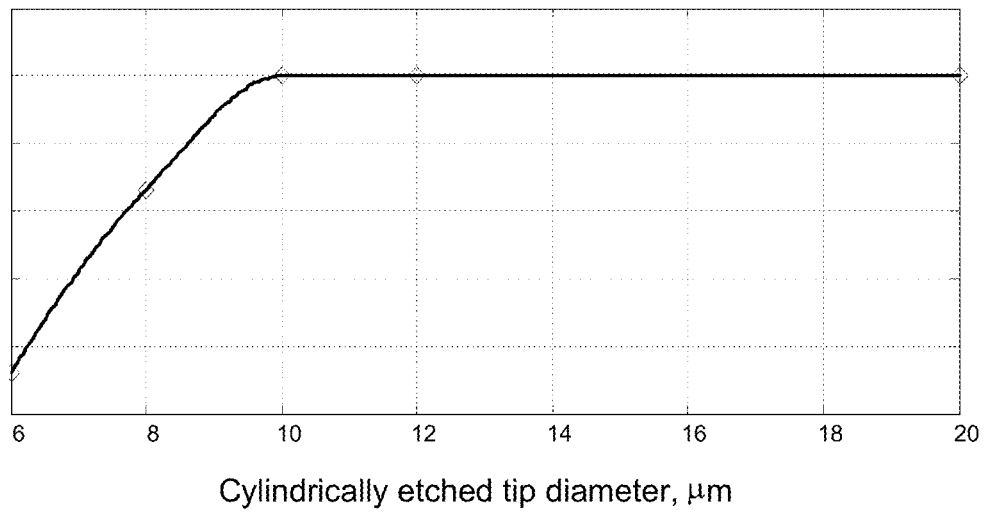

FIG. 7(a) depicts an example of the effect of taper angel on sensitivity for linearly tapered angles (dotted line) and exponentially tapered angles (solid line). The vertical axis of the graph represents an example improvement in sensitivity in logarithmic scale of dB. FIG. 7(b) depicts the effect of fiber diameter of a cylindrically etched fiber on sensitivity. The vertical axis of the graph represents an example improvement in sensitivity in dB. FIG. 7 provides one example of some potential effects from alterations in geometry to the immersion end of a fiber optic hydrophone.

As noted above, it is expected that the fiber optic hydrophones described may be manufactured or used in a variety of manners. As a first example, fiber optic hydrophones may be manufactured optimized for a particular use. Uses include calibration of medical devices. In one example of a calibration, the fiber optic hydrophone disclosed herein may be placed near or in the focal zones of High Intensity Focused Ultrasound (HIFU) fields, High Intensity Therapeutic Ultrasound (HITU) fields, or Lithotripsy devices. The fiber optic hydrophone may be used to calibrate any device used to create HIFU or HITU fields, as well as any other medical ultrasound device, including those used for ultrasound imaging. As another example use, an array of fiber optic hydrophones could be used for imaging. The array may detect signals in a reflective or transmissive mode from a source and may image one or more objects based on the reflections. As another example, the fiber optic hydrophone may be used in sonar applications, to detect changes in pressure in water or to image objects in media. As another example, detection of pressure amplitude may be used in theragnostics, diagnosis, treatment and therapy of a broad range of issues in humans or animals. In one configuration, the hydrophones may be used in situ. In another example, the hydrophones may be used in vivo and in another application, the fiber optic hydrophones described herein may be used in an in vitro application. In another application the optical hydrophone might be used for reception of acoustic/ultrasound pressure from one end of solid barrier to another end in various sealed compartments of military applications of surface vessels, land based rovers, airborne/spaceborne structures.

The device describe herein may be used as a single point fiber optic hydrophone for characterization of one or more acoustic signals. As another example, an array of fiber optic hydrophones described above with respect to FIGS. 2-4 may be provided. The array could be, for example, a linear array comprising two or more fiber optic hydrophones. As another example, a two-dimensional array could be created out of three or more hydrophones. For example, fiber optic hydrophones could be placed in a circular array, a triangular array, a square, a sparse array, a rectangular array or in an amorphous array. Such an array could be used to image or to characterize one or more aspects of an acoustic wave front in an immersion contact medium or a solid.

Figure 8:
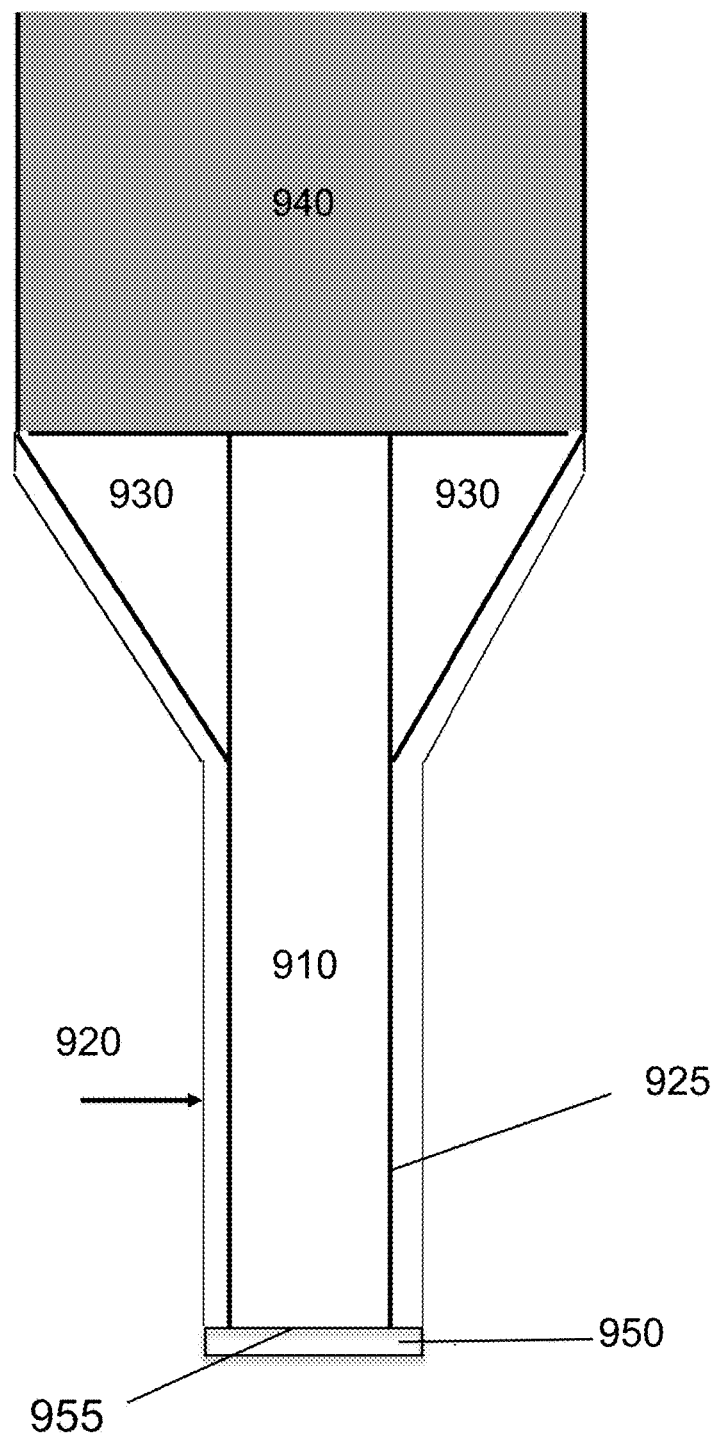
FIG. 8 shows a fiber optic hydrophone tip in an alternate embodiment where the coating covers the side surfaces of the tip and not just the tip end face.

FIG. 8 shows a fiber optic hydrophone tip in an embodiment where the coating 920 covers the tip sides 925 as shown and not just the tip end face 955. The system is constructed of a fiber optic probe 940, wherein the probe has a modified fiber tip 910. The fiber tip 910 is coated with a thin layer of metallic material 920 and 950, acting as partial transparent coating layers. The partial transparency of the coated material facilitates direct interaction between optical signals propagating within the fiber tip 910 and ultrasound waves propagating within the immersion medium outside the fiber tip 910. Interaction is caused by, but is not limited to, acousto-optic effect within the immersion medium as well as within the metallic thin coated layers covering sides 925 and end face 955, in the presence of ultrasound/acoustic waves propagating within the immersion medium. This interaction exists in the immersion medium, between both propagating and non-propagating (evanescent) electromagnetic fields, exist outside the surface of the fiber tip 910, at the side surface 925 and at end face 955, and within the immersion medium. Other nonmetallic coatings may be used as a partial transparent material. The optical fiber 940 may be integrated with a light source, and a signal detection device(s)/system(s).

The shape of the end of the fiber probe 940 can be in a cylindrical shape, for the fiber etched and coated region 920, as shown. It can be in a taper shape 930 or other shapes, based on the required reflective index profile/relationship between the fiber's core-clad-coating and immersion medium. This profile controls the depth of the penetration of evanescent electromagnetic fields into immersion medium. Wherein, evanescent fields are the electromagnetic fields exist outside the optical fiber core 910 for optical signals propagating within the fiber core. In this case, tuning the index profile for the proper relationship can maximize the interaction between optical signals propagating within the fiber probe 940 with the ultrasound waves propagating within the immersion medium. Many fiber probes were manufactured and successfully tested for various applications.

The diameter of the optical fiber tip 910 may be reduced to up to 7 um or less for detection of ultrasound pressures at frequencies up to 100 MHz and more, without the need for spatial averaging correction. The reduction in the diameter of the tip 910 of the fiber 940 can be done gradually in a taper shape 930 or in a sudden change in a cylindrical shape, within a short length of the fiber tip. The short length can range from few micrometers up to few millimeters.

Acousto-optic effects and other interaction phenomena, and/or mechanisms, result in modulating the back reflected optical signals, reflected from the partial transparent coating material. Modulation of back reflected optical signals includes, but not limited to, intensity, phase and/or wavelength modulation. The optical detection device/system may analyze the back reflected signals, and be capable of correlating the demodulated signals with the ultrasound pressure induced in the medium due to the ultrasound waves propagating within the immersion medium. This correlation may be applied for imaging of very small objects, such as cancer tumors, blood vessels, or others, for medical diagnostics or similar applications.

Figure 9:
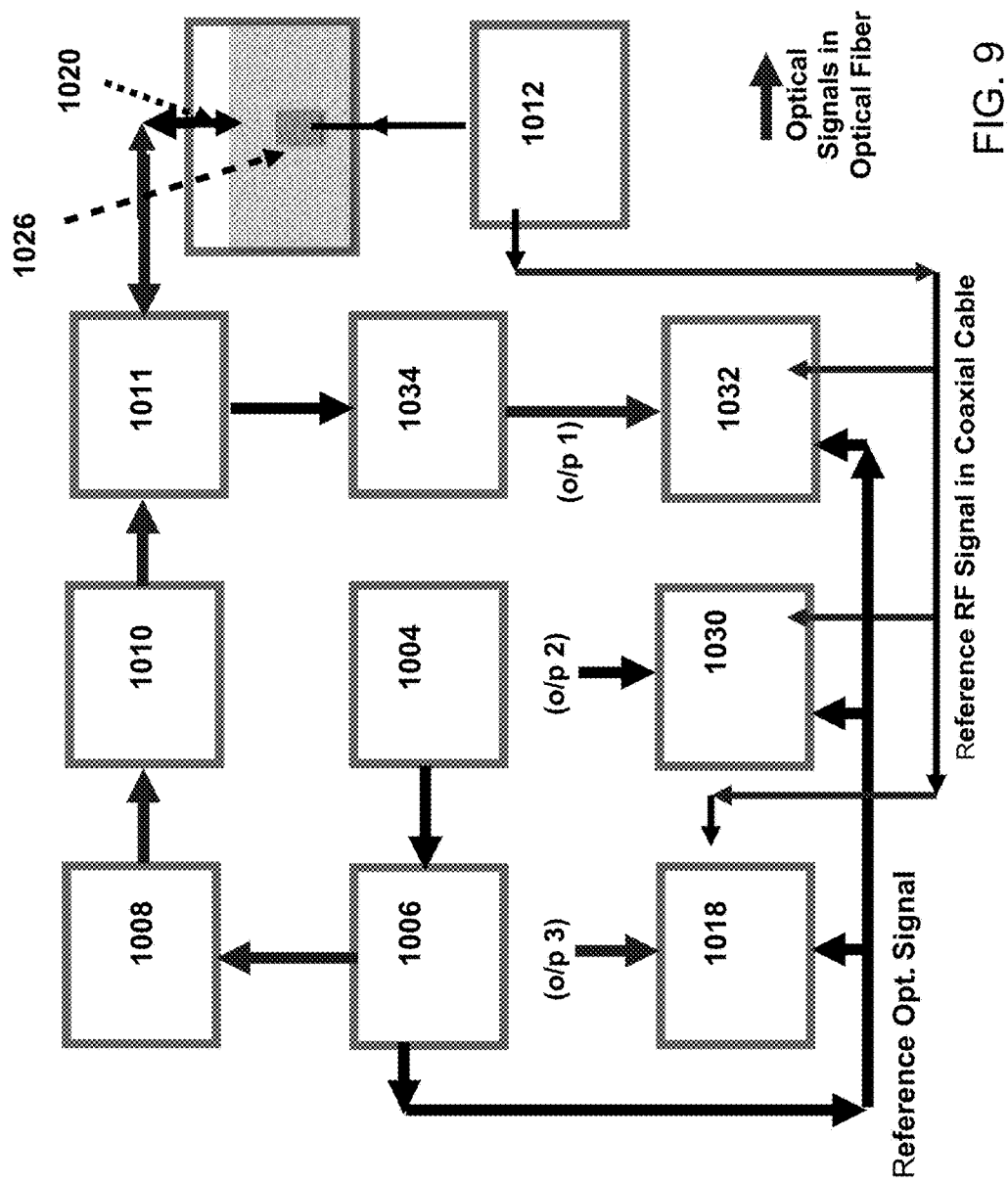
FIG. 9 is a schematic function/block diagram showing some of major components within the developed acousto-optic imaging and/or calibration system.

FIG. 9 shows a schematic function/block diagram of the developed sensory/imaging system similar to that shown in FIG. 2, but with an additional two components, that are used for the demodulation of the acoustic or optical phase and/or wavelength of the detected signals. The diagram is for illustration, and other components can be added in the scope of the function of each component.

FIG. 9 shows a fiber optic hydrophone 1000 that includes an optical probe 1020 in communication with a light source 1004 that is in communication with a fiber optic coupler 1006, optical amplifier and signal conditioner 1008, optical isolator 1010, and optical directional coupler 1011. The optical signal generated by the light source 1004 is transmitted through the coupler 1006, the optical amplifier 1008, the optical isolator 1010, and the optical coupler 1011 to the custom designed fiber probe 1020, as optical hydrophone. Then, the back reflected and modulated signal is directed through the other port of optical directional coupler 1011 to the unit 1034 for optical detection, electrical signal conditioner and processing. The output (o/p) of the conditioner 1034 is directed to three units, for detection and demodulation, as; (o/p 1) unit for signal intensity analysis, (o/p 2) signal phase analysis, and/or (o/p 3) signal wavelength analysis. Wherein the optical and acoustic/ultrasound detection and demodulation units are three units (1032, 1030, and 1018), for the intensity, acoustic/ultrasound and optical phase or/and wavelength analysis and output measurements and evaluation, respectively. The unit 1032 is for the intensity detection and demodulation. The unit 1030 is for the acoustic/ultrasound and optical phase detection and demodulation, wherein different types of phase detection (such as inphase (I) and quadrature phase (Q) channels for down-conversion of acoustic/ultrasound signals or interferometric techniques for optical signals) can be applied. The unit 1018 is for wavelength change' measurement, wherein spectrum analyzers or other devices or techniques can be applied.

A power amplifier and RF generator 1012 generate a signal for transmission through an acoustic/ultrasound generator (i.e., transducer) 1026. Also, a reference RF signal from the RF generator 1012 is directed to the three output units 1030, 1032, and 1018 for signal stability measurements.

All the three units; spectrum analyzer unit 1018, the optical phase demodulation unit 1030, and the intensity demodulation unit 1034 receive a reference optical signal from the light source 1004, through the optical coupler 1006 in addition to acoustic/ultrasound signal from the acoustic/ultrasound generators.

The design of the detection device/system of the developed sensory/imaging system is based on one of the standard stat-of-the-art detection devices/systems required for demodulation of the back reflected signals. The three options of detection devices are shown in the schematic function/block diagram of FIG. 9, wherein, a standard photodetector is used for intensity demodulation 1034 (o/p 1), two optical detectors as I/Q, demodulator for detection of acoustic/ultrasound phase or an interferometric detection system for optical phase demodulation 1030 (o/p 2), and array of photodetectors combined with blazed grating as an optical spectrum analyzer for wavelength change measurements 1018 (o/p 3).

Demodulation of the probe back reflected signals, based on using a partial transparent coating, may result in a very sensitive mechanism for measuring ultrasound pressure in immersion mediums. This method provides a highly sensitive and accurate imaging system with high resolution and a large dynamic range. For micrometer scale imaging, phase and/or wavelength demodulation devices (o/p 2 and o/p 3) will provide the required high sensitivity, accuracy, resolution and a large dynamic range. But they are more expensive and sensitive to environmental impacts. On the other hand, for macro scale imaging, intensity demodulation device is still sensitive, accurate, with high resolution too.

It should be understood that the configurations and/or approaches described herein are exemplary in nature, and that these specific embodiments or examples are not to be considered limiting. The specific routines or methods described herein may represent one or more of any number of strategies. As such, various acts illustrated may be performed in the sequence illustrated, in other sequences, in parallel, or the like. Likewise, the order of the above-described processes may be changed.

Additionally, the subject matter of the present disclosure includes combinations and sub-combinations of the various processes, systems and configurations, and other features, functions, acts, and/or properties disclosed herein, as well as equivalents thereof.

What is claimed is:

1. A system for detecting changes in pressure in an immersion medium or solid, the system comprising:
an optical fiber, wherein the optical fiber has a diameter at an immersion surface contact of the optical fiber of less than 10 um; and
a layer of material deposited on a tip of the fiber, wherein the layer of material is of a thickness of from about 2 nm to about 10 nm;
wherein detecting the pressure in the immersion medium or solid is based on the interaction between evanescent electromagnetic fields that exist outside the optical fiber surface and ultrasound waves propagating in the immersion medium or solid.

2. The system of claim 1 comprising an optical fiber consists of a core and clad, wherein the diameter of the fiber has been reduced to less than 10 um at the fiber tip.

3. The system of claim 1 comprising a layer of material deposited on the tip of the optical fiber, wherein the material is deposited on both the end face and outside of a cylindrical surface of the fiber tip as optical hydrophone.

4. The system of claim 1 further comprising a light source and a detector, wherein the detector measures changes in optical signals based on direct interaction between ultrasound waves with coated materials which impacts reflected optical waves through interactions of waveguiding and evanescent fields at the coated optical fiber interfaces with the immersion medium or solid and indirect interaction with material surrounding through evanescent modes.

5. The system of claim 1 further comprising a computer controller and analyzer that is programmed to relate back reflected optical signals from the tip of the fiber to the changes in acoustic/ultrasound pressure.

6. The system of claim 1 wherein the layer of material is a layer comprising one or more dielectrics.

7. The system of claim 1 wherein the layer of material is a layer comprising one or more of a metal and a dielectric.

8. The system of claim 1 further comprising a light source and a detector, wherein the light source comprises a laser having a wavelength output within a range of from about 500 nm to about 1700 nm.

9. The system of claim 1 wherein the thickness of the layer of material is of from about 3.5 nm to about 8 nm.

10. The system of claim 1 wherein the tip of the fiber comprises a taper angle and a taper length.

11. The system of claim 10 wherein the taper angle is of from about 0 to about 45, and wherein the taper length is of from about 10 um to about 1 mm.

12. The system of claim 1 further comprising a light source and a detector, wherein the detector is configured to detect light back reflected from the layer of material and wherein through interactions of waveguiding and evanescent fields at the coated optical fiber interfaces with immersion medium and indirect interaction with material surrounding through evanescent modes causes changes in light reflected back from the layer of material are measured by the detector.

13. The system of claim 1 further comprising a light source and a detector, wherein the detector is configured to detect light back reflected from the layer of material and wherein changes in light reflected back from the layer of material are measured by phase detection scheme, such as I/Q demodulation and an interferometric system.

14. The system of claim 1 further comprising a light source and a detector, wherein the detector is configured to detect light back reflected from the layer of material and wherein changes in light reflected back from the layer of material are measured by a spectrum analyzer, wherein the detector measures changes in optical signals based on direct impact of ultrasound waves on material and distribution of optical evanescent and waveguiding fields and indirect interaction with material surrounding through evanescent modes.

15. A method for detecting pressure of acoustic or ultrasound waves in an immersion medium or solid, the method comprising:
- contacting the immersion medium or solid with a modified fiber optic including a tip;
- wherein the fiber optic is integrated with a light source and a detector, and
- wherein the fiber optic tip has a diameter of less than 10 um at an immersion surface contact of the fiber optic tip;
- providing a thin layer of material on the fiber optic tip, wherein the thin layer of material is of a thickness in a range of from about 2 nm to about 10 nm; and
- detecting acoustic/ultrasound pressure waves in the immersion medium based on a direct interaction of optical and evanescent electromagnetic fields and ultrasound fields within the fiber optic tip and within the immersion medium.

16. The method of claim 15 wherein the layer of material deposited on the fiber tip is coated and covering on the surface of the fiber tip as well as an end face of the fiber tip.

17. The method of claim 15 wherein the thickness of the layer of material deposited on the fiber tip is adjusted for optimal sensitivity in detecting acoustic waves pressure in immersion medium.

18. The method of claim 15 wherein the optical fiber has a core and a cladding, wherein the cladding is etched/removed away in the fiber tip before coating a thin layer material.

19. The method of claim 15 further comprising detecting an object in the immersion medium by correlating changes in back reflected optical signals and ultrasound pressure in immersion medium.

20. The method of claim 15 wherein a correlation between reflected optical signals and acoustic/ultrasound pressure includes changes in intensity, phase, and wavelength of an optical signal and changes in intensity, phase, and wavelength of acoustic/ultrasound source.

* * * * *